US010722701B2

(12) United States Patent
Ishibe et al.

(10) Patent No.: US 10,722,701 B2
(45) Date of Patent: Jul. 28, 2020

(54) NERVE STIMULATION APPARATUS AND BIOMAGNETIC FIELD MEASUREMENT SYSTEM

(71) Applicants: Takafumi Ishibe, Osaka (JP);
Shigenori Kawabata, Tokyo (JP);
Takumi Yamaga, Kanagawa (JP);
Hiroshi Deguchi, Kanagawa (JP); Koji Yamaguchi, Kanagawa (JP); Shunichi Matsumoto, Kanagawa (JP)

(72) Inventors: Takafumi Ishibe, Osaka (JP);
Shigenori Kawabata, Tokyo (JP);
Takumi Yamaga, Kanagawa (JP);
Hiroshi Deguchi, Kanagawa (JP); Koji Yamaguchi, Kanagawa (JP); Shunichi Matsumoto, Kanagawa (JP)

(73) Assignees: Ricoh Company, Ltd., Tokyo (JP);
National University Corporation Tokyo Medical and Dental University, Tokyo (JP)

( * ) Notice: Subject to any disclaimer, the term of this patent is extended or adjusted under 35 U.S.C. 154(b) by 142 days.

(21) Appl. No.: 15/778,045

(22) PCT Filed: Nov. 7, 2016

(86) PCT No.: PCT/JP2016/004820
§ 371 (c)(1),
(2) Date: May 22, 2018

(87) PCT Pub. No.: WO2017/094221
PCT Pub. Date: Jun. 8, 2017

(65) Prior Publication Data
US 2018/0369568 A1 Dec. 27, 2018

(30) Foreign Application Priority Data

Nov. 30, 2015 (JP) .................................. 2015-232936

(51) Int. Cl.
*A61N 1/04* (2006.01)
*A61B 5/0488* (2006.01)
(Continued)

(52) U.S. Cl.
CPC ........ *A61N 1/0452* (2013.01); *A61B 5/04005* (2013.01); *A61B 5/0488* (2013.01);
(Continued)

(58) Field of Classification Search
CPC .. A61N 1/0452; A61N 1/025; A61N 1/36003; A61N 1/0456; A61B 5/05; A61B 5/04005; A61B 5/407; A61B 5/0488
(Continued)

(56) References Cited

U.S. PATENT DOCUMENTS

| 3,612,061 A | 10/1971 | Collins et al. |
| 8,615,283 B2 | 12/2013 | Besio |

(Continued)

FOREIGN PATENT DOCUMENTS

| JP | 2001-054507 | 2/2001 |
| JP | 2006-271689 | 10/2006 |

(Continued)

OTHER PUBLICATIONS

International Search Report and Written Opinion dated Feb. 7, 2017 in PCT/JP2016/004820 filed on Nov. 7, 2016.
(Continued)

*Primary Examiner* — Amanda K Hulbert
*Assistant Examiner* — Philip C Edwards
(74) *Attorney, Agent, or Firm* — Oblon, McClelland, Maier & Neustadt, L.L.P.

(57) ABSTRACT

A nerve stimulation apparatus is provided. The nerve stimulation apparatus detects nerve activities from a body surface and applies stimulation. The nerve stimulation apparatus includes a stimulation apparatus with multiple electrodes
(Continued)

which are arranged on skin and a current supply unit which supplies a current to the electrodes, which stimulation apparatus provides the current to a living body percutaneously to stimulate a target nerve; a measurement apparatus which measures activities of muscles governed by the nerve according to the stimulation from the stimulation apparatus; and an information processing apparatus which determines, based on a measurement result of the nerve activities obtained from the measurement apparatus, which electrode is capable of providing the target nerve activities equal to or greater than a desired value.

8 Claims, 12 Drawing Sheets

(51) Int. Cl.
  A61N 1/36    (2006.01)
  A61B 5/04    (2006.01)
  A61B 5/00    (2006.01)
  A61B 5/05    (2006.01)
  A61N 1/02    (2006.01)

(52) U.S. Cl.
  CPC ............... *A61B 5/05* (2013.01); *A61B 5/407* (2013.01); *A61N 1/025* (2013.01); *A61N 1/0456* (2013.01); *A61N 1/36003* (2013.01)

(58) Field of Classification Search
  USPC .......................................................... 607/48
  See application file for complete search history.

(56) References Cited

U.S. PATENT DOCUMENTS

| 9,616,224 | B2 | 4/2017 | Bulsen et al. |
| 2010/0004715 | A1* | 1/2010 | Fahey ................. A61N 1/0456 607/48 |
| 2012/0226330 | A1* | 9/2012 | Kolen .................... A61H 39/02 607/48 |
| 2013/0030277 | A1 | 1/2013 | Fahey |
| 2014/0012133 | A1 | 1/2014 | Sverdlik et al. |
| 2014/0343392 | A1 | 11/2014 | Yang |
| 2015/0238104 | A1* | 8/2015 | Tass ..................... A61N 1/3605 600/409 |

FOREIGN PATENT DOCUMENTS

| JP | 2013-509251 | | 3/2013 |
| JP | 2013-509905 | A | 3/2013 |
| JP | 2013-514146 | A | 4/2013 |
| JP | 2014-133123 | | 7/2014 |
| JP | 2014-200384 | | 10/2014 |
| JP | 2015-525579 | | 9/2015 |
| JP | 2017-015620 | | 1/2017 |
| WO | WO 2011/084450 | A1 | 7/2011 |
| WO | WO 2013/011474 | A2 | 1/2013 |

OTHER PUBLICATIONS

Extended European Search Report dated Oct. 15, 2018 in Patent Application No. 16870164.7.
Office Action dated Dec. 3, 2019 in Japanese Patent Application No. 2015-232936.

* cited by examiner

[Fig. 1]
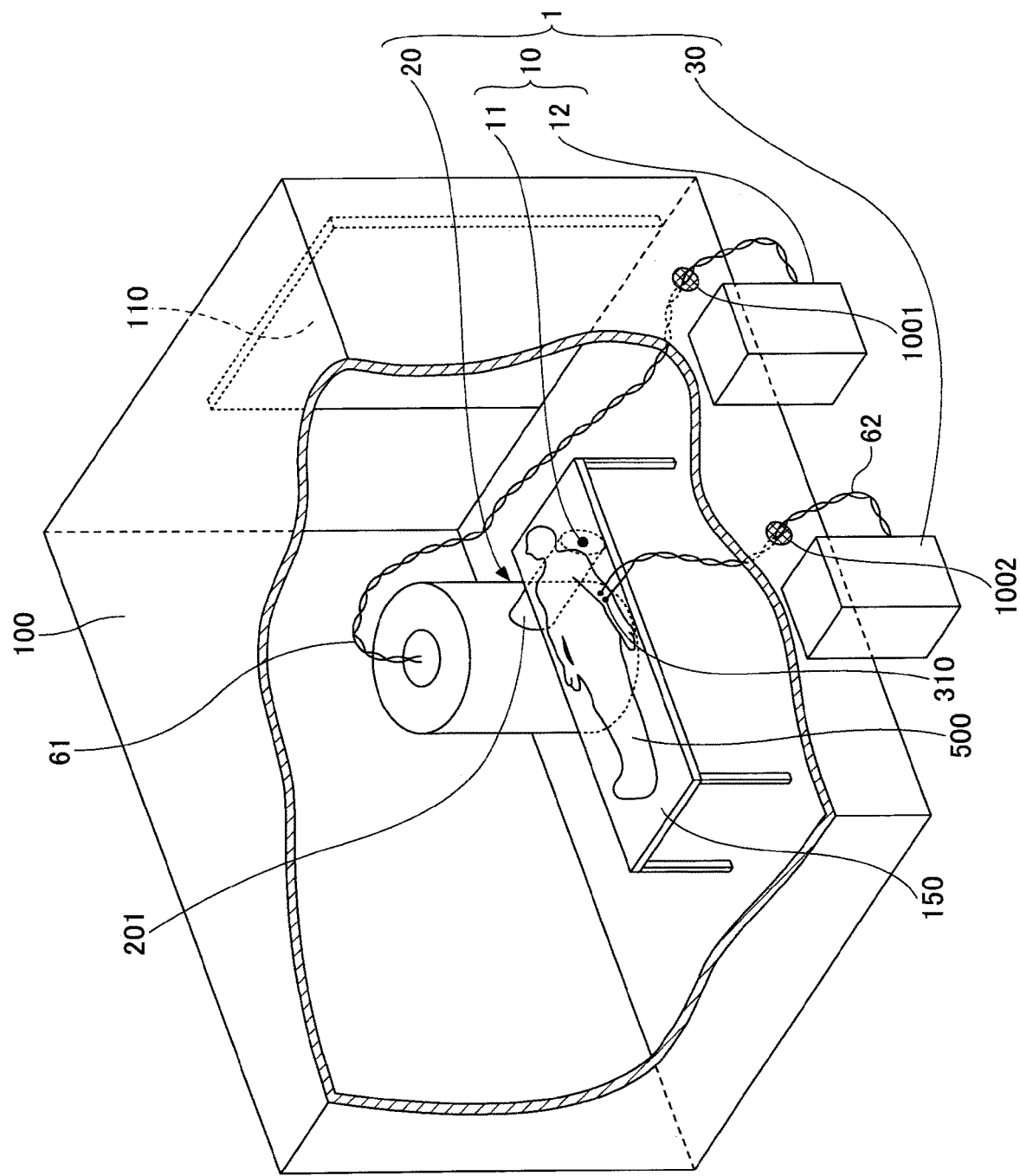

[Fig. 2]
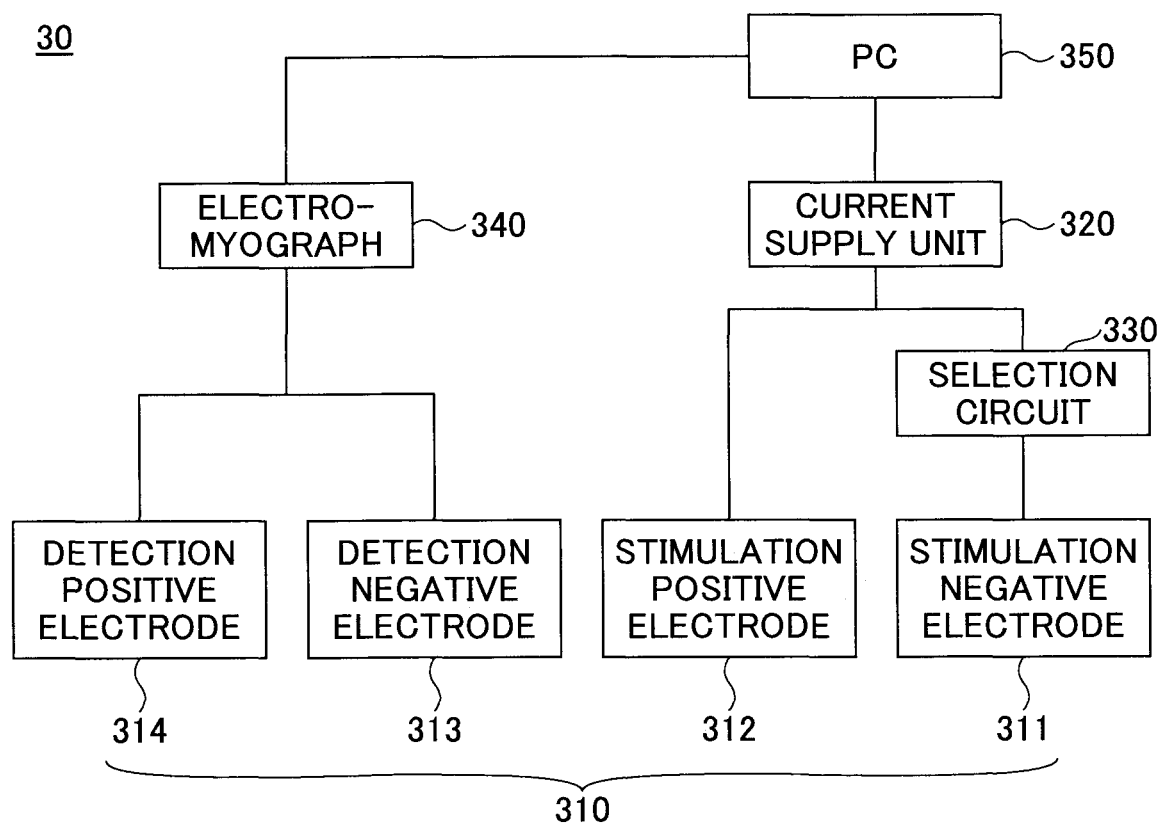

[Fig. 3]
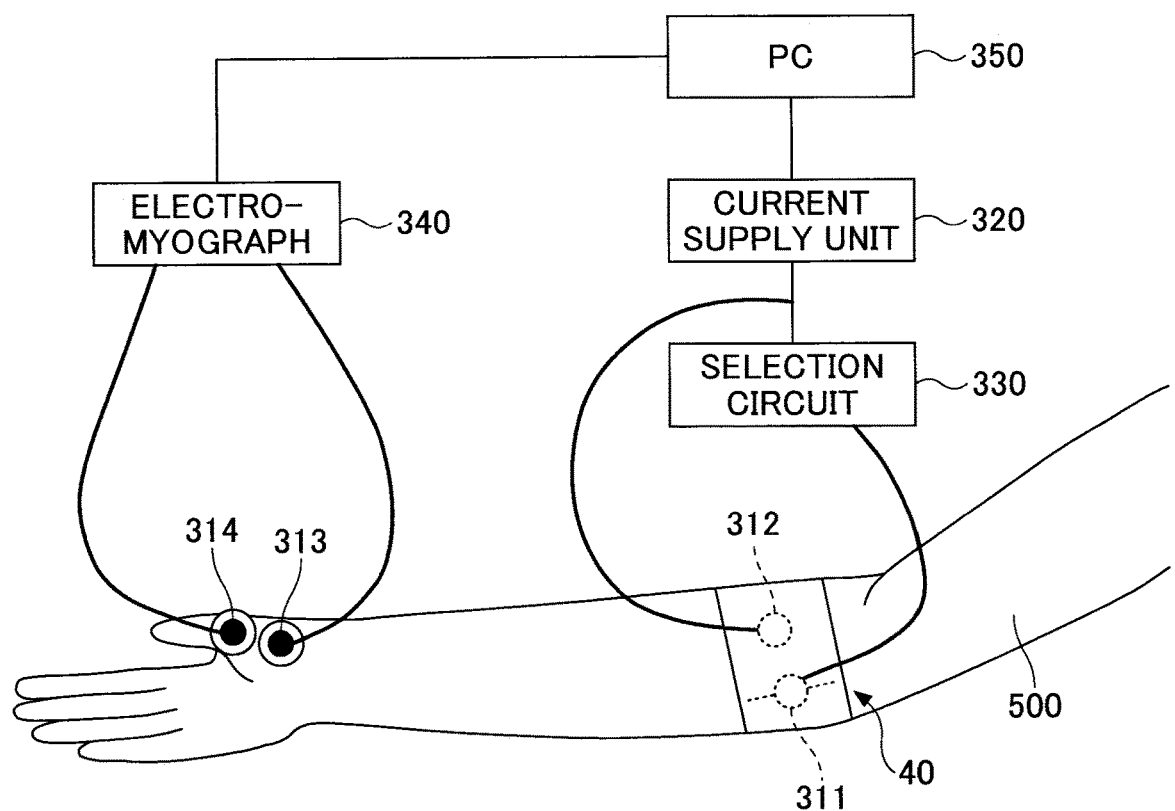

[Fig. 4]
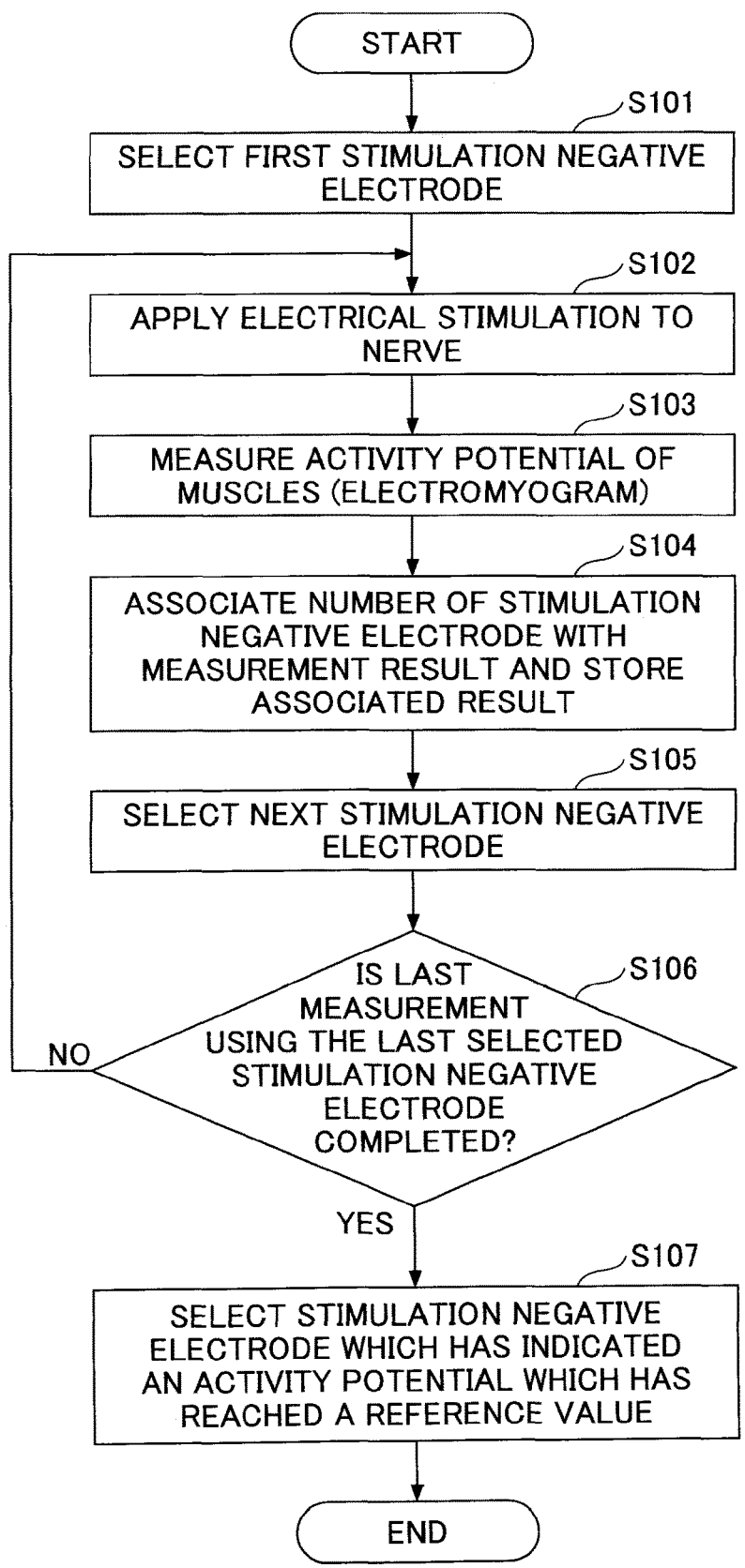

[Fig. 5A]
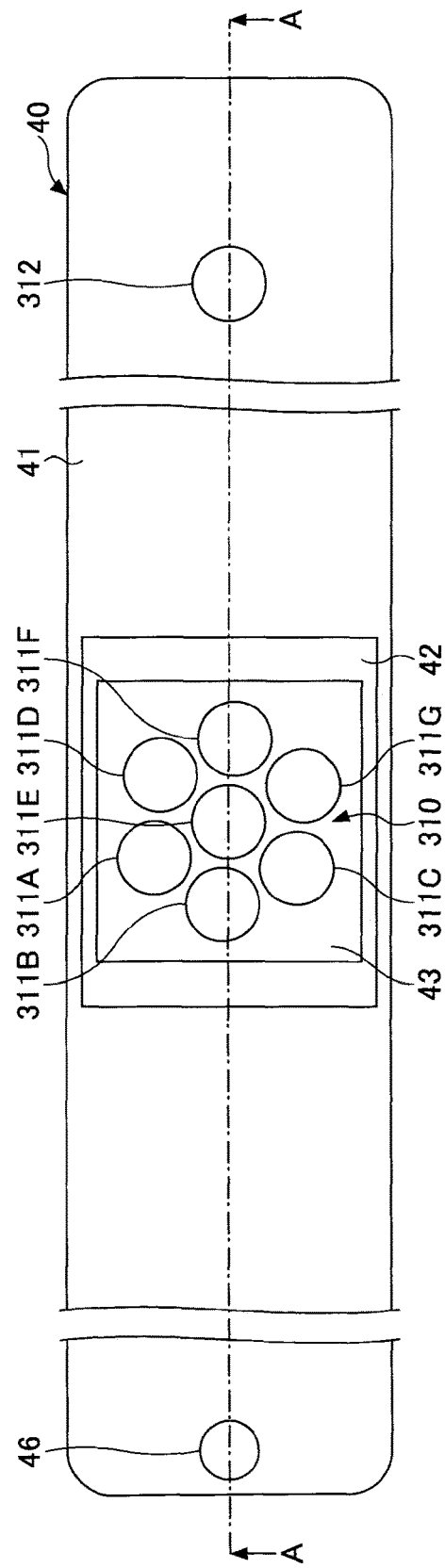

[Fig. 5B]
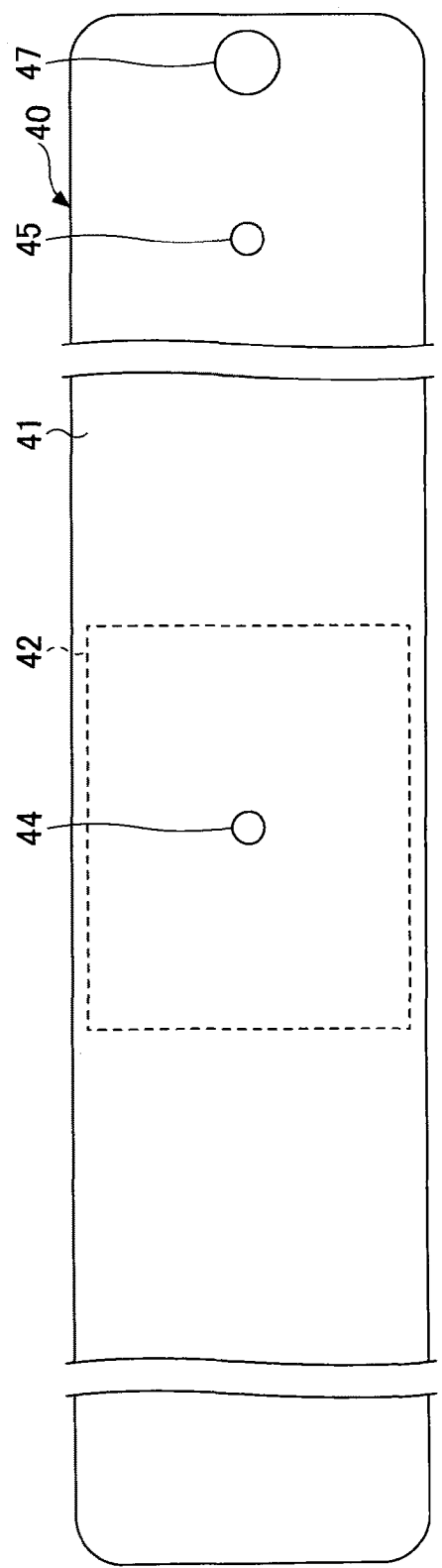

[Fig. 5C]
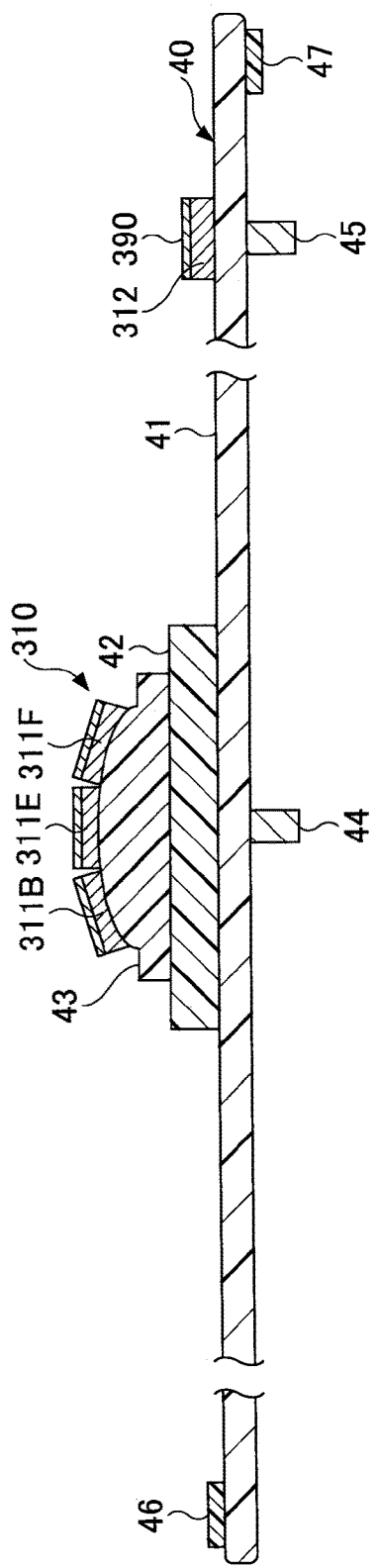

[Fig. 6]
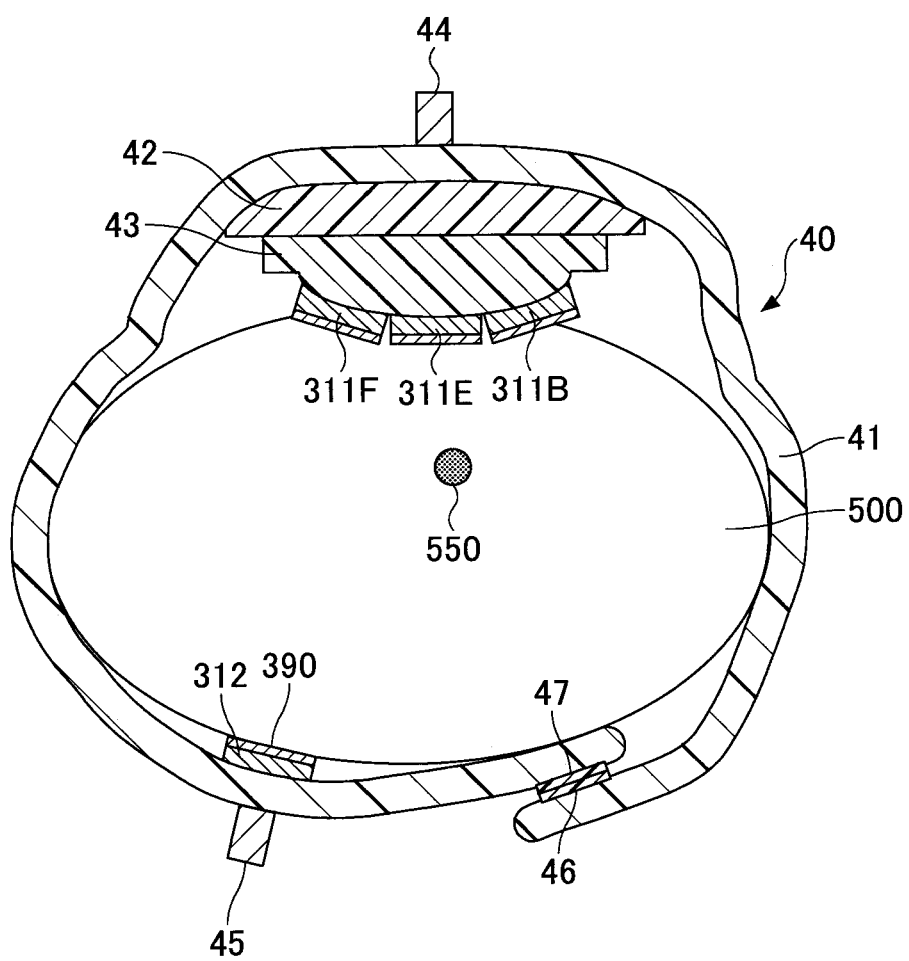

[Fig. 7A]
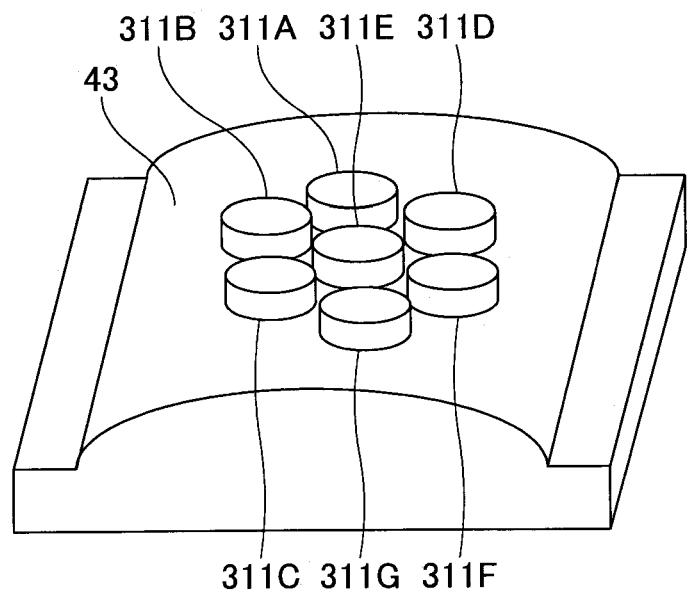
[Fig. 7B]
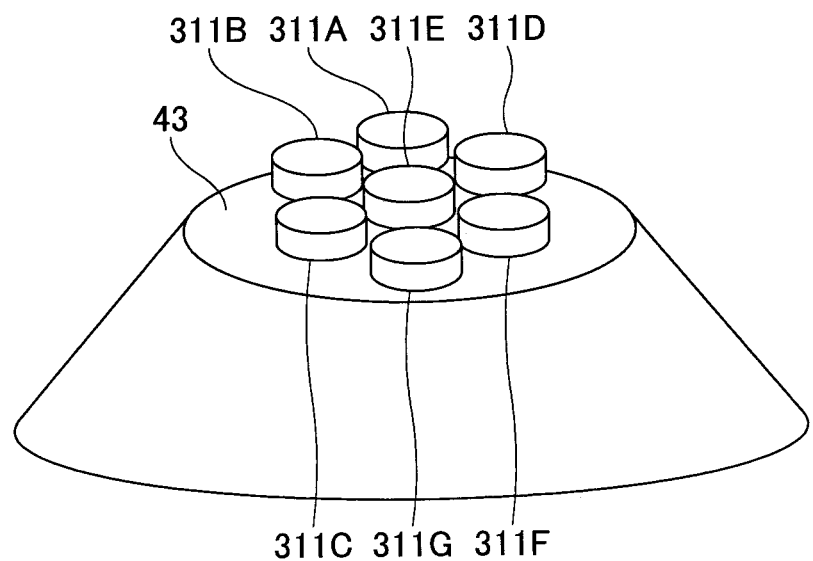

[Fig. 8]
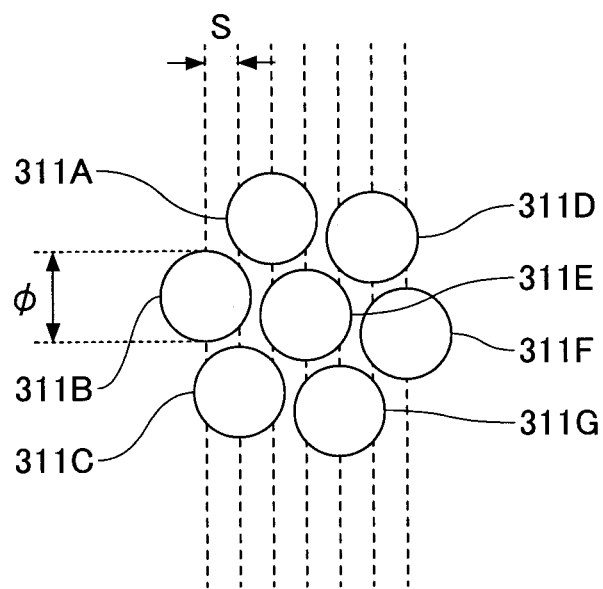
[Fig. 9]
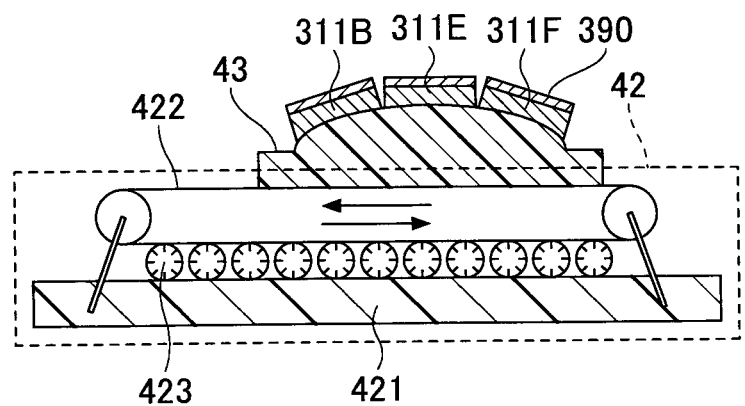

[Fig. 10A]
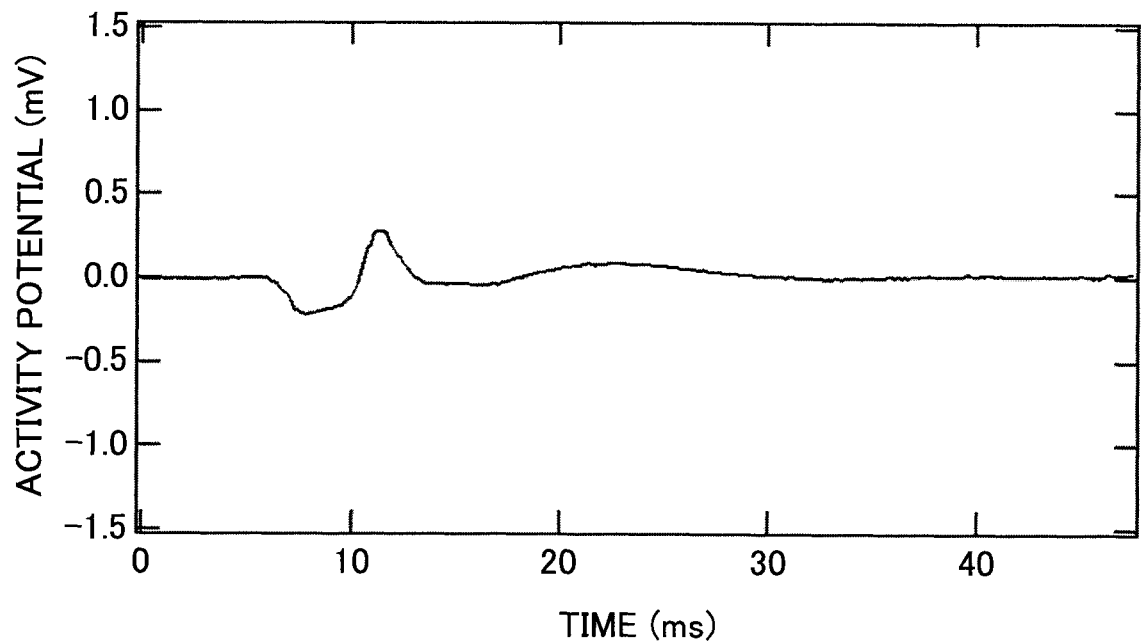
[Fig. 10B]
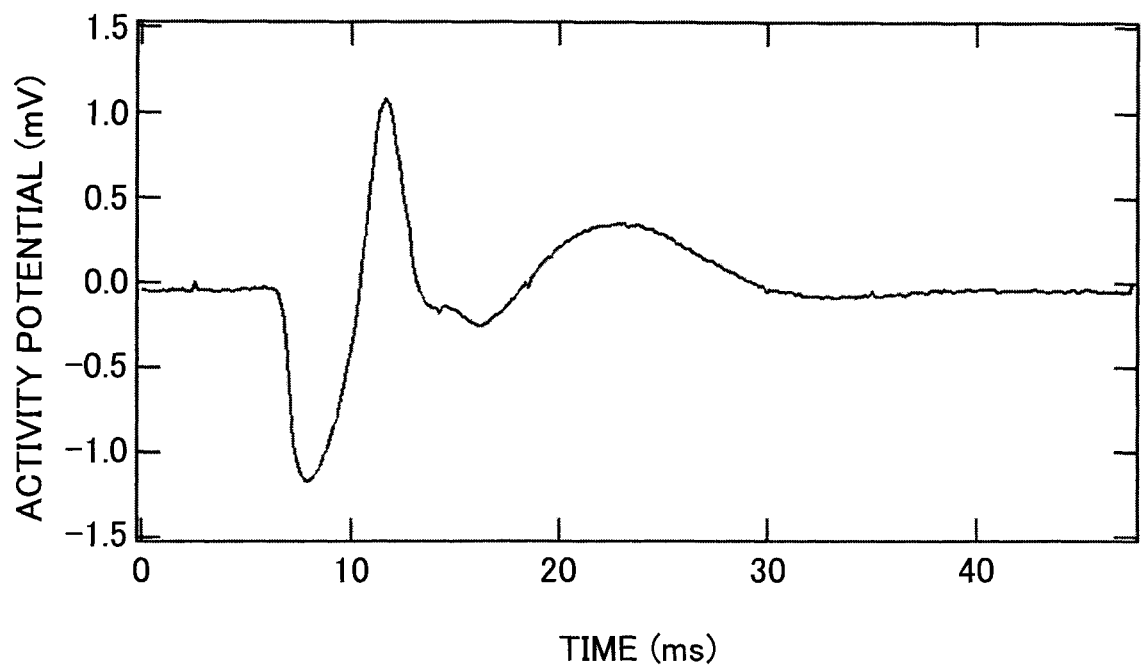

[Fig. 11]
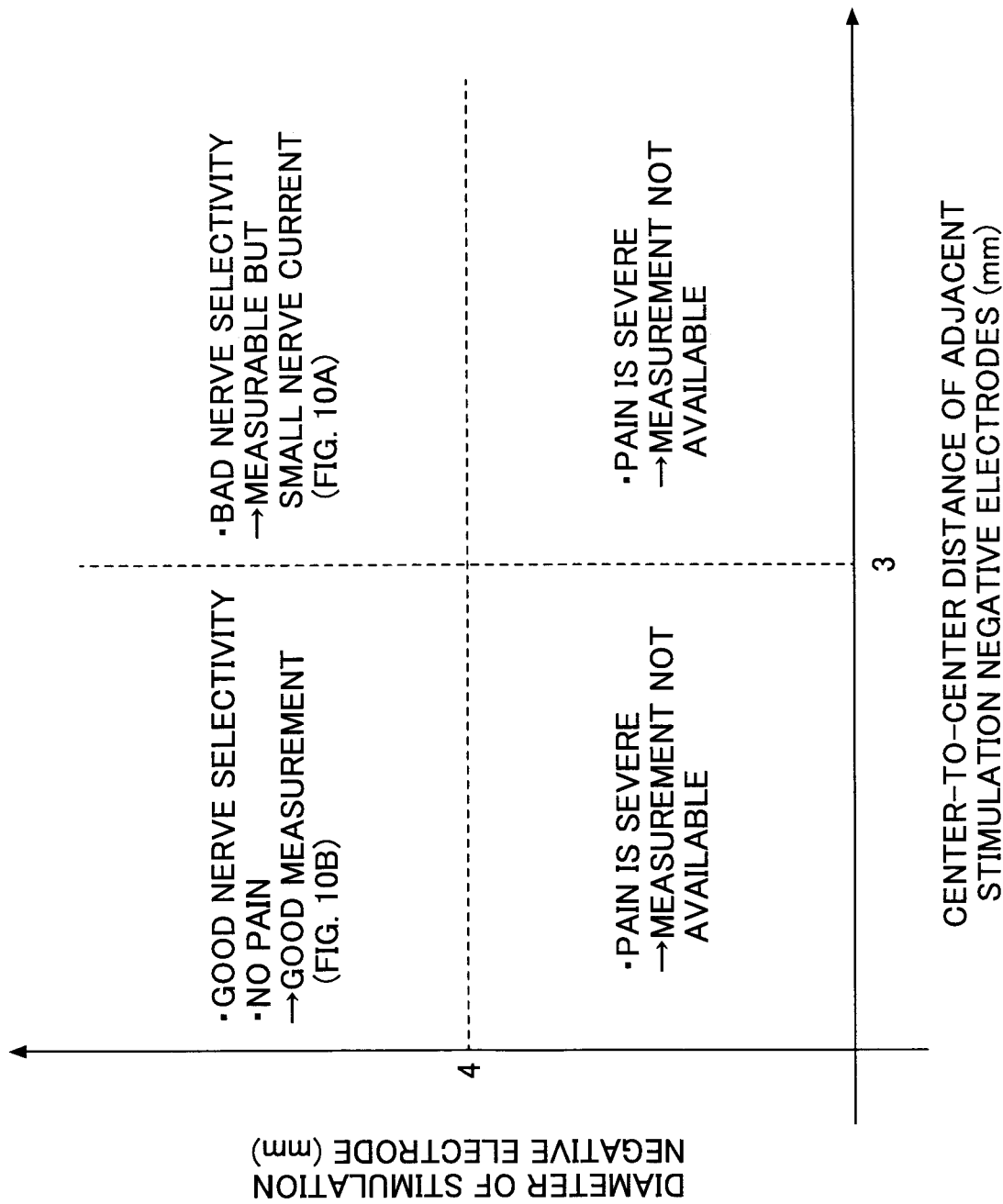

NERVE STIMULATION APPARATUS AND BIOMAGNETIC FIELD MEASUREMENT SYSTEM

TECHNICAL FIELD

The present invention relates to a nerve stimulation apparatus and a biomagnetic field measurement system.

BACKGROUND ART

In recent years, according to the progress of diagnostic imaging apparatuses including magnetic resonance imaging (MRI), etc., it has become easy to perform diseased portion diagnosis of the spinal cord and peripheral nerves due to oppression lesions. However, there are many cases, for example, in which no symptom is found even when there is apparently an oppression according to an image. Therefore, it is impossible to truly diagnose a functionally diseased portion of the spinal cord or the peripheral nerves by using only morphological information based on images, and thus, nerve function diagnostics using electrophysiological techniques are still indispensable tests.

In order to perform detailed diseased portion diagnosis, it is the best way to measure a nerve evoked potential by using the inching technique. However, because an electrical current receives strong influence from surrounding tissue in nerves deep inside away from the body surface, especially in the spinal cord, it is difficult to accurately evaluate nerve functions from the body surface. Therefore, the spinal cord evoked potential is measured by intraoperatively setting electrodes near the spinal cord, or by preoperatively and percutaneously inserting catherter electrodes in the extradural space or the subarachnoid space. Inserting the catherter electrodes is invasive and requires skill, and cannot be considered as a test which can be easily performed for diagnosis. Therefore, a non-invasive and easy electrophysiological technique is desired.

It should be noted that, when currents flow, magnetic fields are generated around the currents in accordance with the right-handed screw rule. The magnetic field has a property of receiving almost no influence from the biological tissue such as bones and soft tissue, and it is known that theoretically the biomagnetic field measurement has higher spatial accuracy compared to the potential measurement. The biomagnetic field measurement is a technique for measuring, from outside of a living body, microscopic magnetic fields generated according to activities of nerves and muscles of the living body, and analyzing the behavior of the activity sources. A biomagnetic field measurement system has been developed and introduced to medical sites in which system a multi-channel magnetic measurement apparatus utilizing superconducting quantum interference devices (SQUID) is used.

Currently, the biomagnetic field measurement has been especially applied to the field of brain research, and thus, brain activities have been identified with high spatial accuracy. Further, medical sites of mainly spine/spinal cord surgery and peripheral nerve surgery have been paying attention to the biomagnetic field measurement system as an effective technique for diagnosing a nerve signal propagation disorder in the case of occurrence of a nervous system disorder by measuring magnetic fields according to activities of the nervous system other than the brain such as the spinal cord and peripheral nerves. It should be noted that several papers are known in which experimental examples of measuring the spinal cord evoked magnetic fields are described.

In order to measure nerve magnetic fields of a living body, a nerve stimulation apparatus is needed together with the magnetic measurement apparatus. The peripheral nerves are stimulated by stimulation currents according to the nerve stimulation apparatus, and magnetic fields generated by nerve activities due to the stimulation are measured by the magnetic field measurement apparatus. By synchronizing the magnetic field measurement with the current stimulation, the measured magnetic fields can be identified as generated by the currents flowing in the peripheral nerves and the spinal cord. However, it is difficult to apply stable stimulation currents to the peripheral nerves. For example, a subtle change of positional relationship between nerves and stimulation electrodes disables an appropriate peripheral nerve stimulation, and thus, it becomes difficult to apply optimal peripheral nerve stimulation, which is a problem.

Therefore, a technique has been studied in which multiple stimulation negative electrodes and a circuit for selecting the best electrode of the electrodes are used. In the technique, an electrode should be selected which stimulates the nerve appropriately, and the nerves should be stimulated with high efficiency (e.g., refer to PTL 1). With the above technique, it is possible to realize a nerve stimulation apparatus which percutaneously applies optimal stimulation to the nerves.

CITATION LIST

Patent Literature

[PTL 1] Japanese Unexamined Patent Application Publication No. 2006-271689

SUMMARY OF INVENTION

Solution to Problem

A nerve stimulation apparatus is provided. The nerve stimulation apparatus detects nerve activities from a body surface and applies stimulation. The nerve stimulation apparatus includes a stimulation apparatus with multiple electrodes which are arranged on skin and a current supply unit which supplies a current to the electrodes, which stimulation apparatus provides the current to a living body percutaneously and stimulates a target nerve; a measurement apparatus which measures activities of muscles governed by the nerve according to the stimulation by the stimulation apparatus; and an information processing apparatus which determines, based on a measurement result of the nerve activities obtained from the measurement apparatus, which electrode is capable of providing the target nerve activities equal to or greater than a desired value.

Advantageous Effects of Invention

According to an embodiment, it is possible to provide a nerve stimulation apparatus whose accuracy of selecting a nerve stimulation electrode is improved.

BRIEF DESCRIPTION OF DRAWINGS

FIG. 1 is a drawing illustrating a spinal cord evoked magnetic field measurement system.

FIG. 2 is a drawing illustrating an example of a nerve stimulation apparatus.

FIG. 3 is a schematic diagram illustrating an example of a state in which electrodes of the nerve stimulation apparatus are attached to a part of a subject's body.

FIG. 4 is a flowchart illustrating an operation of the nerve stimulation apparatus in the state of FIG. 3.

FIG. 5A is a drawing illustrating an example of a structure of an attachment unit to be attached to the subject.

FIG. 5B a drawing illustrating an example of a structure of an attachment unit to be attached to the subject.

FIG. 5C is a drawing illustrating an example of a structure of an attachment unit to be attached to the subject.

FIG. 6 is a cross-sectional view illustrating an example of a state in which the attachment unit is attached to the subject.

FIG. 7A is a perspective view illustrating an example of a specific structure of a three-dimensional structure.

FIG. 7B is a perspective view illustrating an example of a specific structure of a three-dimensional structure.

FIG. 8 is a plan view illustrating an example of an arrangement of stimulation negative electrodes.

FIG. 9 is a cross-sectional view illustrating an example of a specific structure of a movable unit.

FIG. 10A is a drawing illustrating measurement result examples of a maximum myoelectric signal.

FIG. 10B is a drawing illustrating measurement result examples of a maximum myoelectric signal.

FIG. 11 is a drawing illustrating an example of a relationship between myoelectric measurement and the stimulation negative electrodes when electrical stimulation was applied to the subject's arm.

DESCRIPTION OF EMBODIMENTS

The present invention has been made in view of the above, and an object is to provide a nerve stimulation apparatus whose accuracy of selecting the nerve stimulation electrode is improved.

In the following, referring to the drawings, an embodiment will be described. It should be noted that, in each of the drawings, the same numeral is assigned to the same element and a duplicated description may be omitted.

(Spinal Cord Evoked Magnetic Field Measurement System)

In an embodiment, an example is shown in which a nerve stimulation apparatus is used for a spinal cord evoked magnetic field measurement system as a biomagnetic field measurement system. FIG. 1 is a drawing illustrating a spinal cord evoked magnetic field measurement system 1.

Referring to FIG. 1, the spinal cord evoked magnetic field measurement system 1 includes as main elements a magnetism measurement apparatus 10, a cryogenic container 20, and a nerve stimulation apparatus 30. The nerve stimulation apparatus 30 is an apparatus for applying electrical stimulation to a nerve from a body surface. The magnetism measurement apparatus 10 includes a SQUID sensor array 11 and a signal processing unit 12, and measures magnetic fields evoked in the living body by the electrical stimulation of the nerve stimulation apparatus 30.

A part of the spinal cord evoked magnetic field measurement system 1 is arranged in a magnetism shielded room 100. The reason why the magnetism shielded room 100 is used is for measuring a spinal cord evoked magnetic field which is a weak magnetic field generated by the living body. The magnetism shielded room 100 can be constructed by, for example, laminating plates made of permalloy, etc., which is a high magnetic permeability material, and plates made of conductors such as copper and aluminum.

The magnetism shielded room 100 has, for example, an internal space as big as about 2.5 m by 3.0 m by 2.5 m, and includes a door 110 which enables transporting equipment and instruments, and enables people going in and out. Similar to other parts of the magnetism shielded room 100, the door 110 can be constructed by laminating plates made of permalloy, etc., which is a high magnetic permeability material, and plates made of conductors such as copper and aluminum.

It should be noted that, in this specification, the high magnetic permeability material refers to a material whose relative permeability is greater than 1000. As high magnetic permeability materials, other than the permalloy, a simple substance of iron, nickel, or cobalt, alloy of iron, nickel, or cobalt (including amorphous alloy, powder, nanoparticles), ferrite, etc., can be listed.

In the following, the spinal cord evoked magnetic field measurement system 1 and its peripheral parts will be described in further detail. In the magnetism shielded room 100, a table 150 is arranged. Further, in the magnetism shielded room 100, the cryogenic container 20 is arranged, and a signal line 61 used for measurement, control, etc., is connected to the SQUID sensor array 11 in the cryogenic container 20. The signal line 61 includes a twisted cable, etc., for reducing magnetic field noise, and is, through a hole 1001 opened in the magnetism shielded room 100, pulled out of the magnetism shielded room 100, and connected to a signal processing unit 12 included in the magnetism measuring apparatus 10.

In the measurement using the spinal cord evoked magnetic field measurement system 1, a subject 500 lies on his/her back on the table 150 in the magnetism shielded room 100, and the spinal cord evoked magnetic field measurement is performed while the subject 500 is in a resting state. By performing the measurement while the subject 500 is in a resting state, it is possible, not only to reduce the burden on the subject 500, but also to reduce a positional gap between the subject 500 and the measuring apparatus due to unnecessary movement of the subject 500, and reduce magnetic field noise, etc., from muscles generated by muscle tension.

The cryogenic container 20 is also referred to as a dewar, and retains liquid helium necessary for a cryogenic operation of the SQUID sensor array 11 which detects magnetic fields generated from a living body. The cryogenic container 20 includes, for example, a protrusion unit 201 adapted to the spinal evoked magnetic field measurement, and the SQUID sensor array 11 is arranged inside the protrusion unit 201.

It is possible to perform spinal cord evoked magnetic field measurement in a state in which a cervical spine or a lumbar spine of the subject 500 lying on his/her back is in contact with the protrusion unit 201 inside which is the SQUID sensor array 11.

When measuring the spinal cord evoked magnetic field, it is necessary to intentionally provoke nervous activities by using electrical stimulation. Therefore, electrical stimulation is applied to the subject 500 by using the nerve stimulation apparatus 30. Specifically, the nerve stimulation apparatus 30 includes an electrode 310, the electrode 310 is attached to a part of the body of the subject 500, and the electrical stimulation is applied to the subject 500. The electrode 310 includes at least stimulation positive electrodes and stimulation negative electrodes, and is attached onto a part of the skin where electrical stimulation can be efficiently applied to the median nerve of the elbow joint, the peroneal nerve of the knee joint, etc., of the subject 500.

A signal line 62 for transmitting stimulation is attached to the electrode 310. The signal line 62 includes a twisted cable, etc., for reducing magnetic field noise. The signal line 62 is, through a hole 1002 opened in the magnetism shielded room 100, pulled out of the magnetism shielded room 100, and connected to a body (a part other than the electrode 310) of the nerve stimulation apparatus 30 arranged out of the magnetism shielded room 100. The details of the electrode 310 will be described later.

In order to provoke nervous activities of the subject 500, the electrical stimulation apparatus 30 can cause a pulse-shaped current to flow between the stimulation positive electrodes and the stimulation negative electrodes of the electrode 310. Regarding the electrical stimulation at the time of spinal cord evoked magnetic field measurement, for example, a pulse current of about a few mA is applied at a few Hz. Magnetic fields from the spinal cord, caused by the nerve activities evoked by the electrical stimulation, are detected by the SQUID sensor array 11.

In the spinal cord evoked magnetic field measurement system 1, the current used for the electrical stimulation at the time of applying the electrical stimulation is itself magnetic field noise. Specifically, the magnetic field, generated by the pulse current which flows in the signal line 62 from the electrical stimulation apparatus 30 to the electrode 310 and flows between the stimulation positive electrodes and the stimulation negative electrodes of the electrode 310, goes into the SQUID sensor array 11 and becomes noise.

The magnetic noise generated by the signal line 62 is reduced by use of twisted cable and optical transmission. However, the magnetic noise generated by the pulse current flowing between the stimulation positive electrodes and the stimulation negative electrodes of the electrode 310 cannot be reduced by the use of twisted cable and optical transmission. Therefore, in order to reduce the magnetic field noise generated by the pulse current used for the electrical stimulation and in order to measure the spinal cord evoked magnetic field more accurately, the vicinity of the electrode 310 attached onto a part of the body of the subject 500 may be covered by a magnetism blocking cover made of high magnetic permeability material such as the permalloy.

(Nerve Stimulation Apparatus)

Overview and Operation of Nerve Stimulation Apparatus

Next, the nerve stimulation apparatus 30 will be described in detail. FIG. 2 is a drawing (block diagram) illustrating an example of a nerve stimulation apparatus 30. As illustrated in FIG. 2, the nerve stimulation apparatus 30 includes the electrode 310, a current supply unit 320, a selection circuit 330, an electromyograph 340, and a personal computer (PC) 350.

The electrode 310 includes a stimulation negative electrode 311, a stimulation positive electrode 312, a detection negative electrode 313 and a detection positive electrode 314, which are arranged on the skin. The stimulation negative electrode 311 is a negative side electrode of the stimulation electrode for provoking nerve activities by electrical stimulation. Multiple stimulation negative electrodes 311 are provided. The stimulation positive electrode 312 is a positive side electrode of the stimulation electrode for provoking nerve activities by electrical stimulation. The detection negative electrode 313 is a negative side electrode of the detection electrode for measuring an activity potential of muscles (electromyogram) by using the electromyograph 340. The detection positive electrode 314 is a positive side electrode of the detection electrode for measuring an activity potential of muscles by using the electromyograph 340.

The current supply unit 320 is a circuit for, for example, supplying a stimulation current to one of the stimulation negative electrodes 311 selected by the selection circuit 330. The selection circuit 330 selects a stimulation negative electrode 311 from the multiple stimulation negative electrodes 311. It should be noted that, if necessary, the selection circuit 330 may select multiple stimulation negative electrodes 311, and the current supply unit 320 may supply stimulation currents to the multiple stimulation negative electrodes 311 selected by the selection circuit 330, simultaneously.

As described above, a stimulation apparatus for percutaneously applying electrical stimulation to a nerve of a living body can be realized by the current supply unit 320, the selection circuit 330, the stimulation negative electrodes 311, and the stimulation positive electrodes 312.

The electromyograph 340 is an apparatus for measuring an activity potential between the detection negative electrode 313 and the detection positive electrode 314. It should be noted that an apparatus other than the electromyograph may be used as long as the apparatus is capable of measuring activities of muscles governed by the nerve stimulated by the above stimulation apparatus. For example, an acceleration sensor, a motion sensor, etc., may be used. Further, the activities of muscles governed by the nerve may not be measured. An activity potential of the stimulated nerve itself (nerve evoked potential) may be measured by the detection electrode from the body surface.

The PC 350 is an information processing apparatus which receives measurement results of the muscle activities from the measurement apparatus such as the electromyograph 340, etc., and determines a stimulation electrode which generates the largest muscle activities. The PC 350 can transmit and receive instructions and data to and from the current supply unit 320, the selection circuit 330, and the electromyograph 340. The PC 350 may include, for example, a central processing unit (CPU), a read only memory (ROM), a random access memory (RAM), a main memory, etc.

In this case, various functions of the PC 350 can be realized by having a program stored in the ROM, etc., read into the main memory and executed by the CPU. The CPU of the PC 350 can read and write data from and to the RAM, if necessary. It should be noted that a part or all of the PC 350 may be realized only by hardware. Further, the PC 350 may physically consist of multiple apparatuses. Further, the PC 350 may include a hard disk apparatus, an optical disk apparatus, etc.

FIG. 3 is a schematic diagram illustrating an example of a state in which electrodes of the nerve stimulation apparatus are attached to a part of the body of the subject 500. FIG. 4 is a flowchart illustrating an operation of the nerve stimulation apparatus in the state of FIG. 3.

In FIG. 3, the multiple stimulation negative electrodes 311 mounted on an attachment unit 40 (details will be described later by referring to FIG. 5 and FIG. 6) are arranged in contact with the skin of the subject 500, and are connected to the selection circuit 330. Further, the stimulation positive electrode 312 mounted on the attachment unit 40 is arranged in contact with the skin of the subject 500, and is connected to the current supply unit 320. Further, the detection negative electrode 313 and the detection positive electrode 314 are arranged in contact with the skin of the subject 500, and are connected to the electromyograph 340.

After the state of FIG. 3, as illustrated in FIG. 4, first, in step S101, the PC 350 transmits an instruction to the selection circuit 330 and selects one of the stimulation negative electrodes 311 as a first stimulation negative electrode. Next, in step S102, the PC 350 transmits an instruction to the current supply unit 320, and applies electrical stimulation to the nerve by providing a stimulation current between the selected stimulation negative electrode 311 and the stimulation positive electrode 312.

Next, in step S103, the electromyograph 340 measures an activity potential of muscles generated between the detection negative electrode 313 and the detection positive electrode 314. The activity potential of muscles measured by the electromyograph 340 is transmitted to the PC 350. Next, in step S104, the PC 350 associates a number of the selected stimulation negative electrode 311 with the measurement result (measured activity potential of muscles), and stores the associated result in the RAM, etc. Next, in step S105, the PC 350 transmits an instruction to the selection circuit 330, and selects the next one of the stimulation negative electrodes 311.

Next, in step S106, the PC 350 determines whether the last measurement, in which the one selected last from the stimulation negative electrodes 311 is used, has been completed. In the case where the PC 350 determines that the last measurement has not been completed in step S106 (in the case of NO), the step returns to step S102 and the processes described above will be repeated. On the other hand, in the case where the PC 350 determines that the last measurement has been completed in step S106 (in the case of YES), the step moves to step S107.

Next, in step S107, the PC 350 determines which stimulation negative electrodes 311 have indicated activity potentials which have reached a reference value based on the data of the selected stimulation negative electrodes and the corresponding measured activity potentials of muscles stored in the RAM, etc. Afterwards, when measuring the spinal cord evoked magnetic field, the determined stimulation negative electrodes 311 will be selected. It should be noted that, if necessary, processes of FIG. 4 will be performed again, and the stimulation negative electrodes 311 may be selected again. As an example of "if necessary", a case where the position of the attachment unit 40 is shifted, etc., can be listed.

Structure Example of Attachment Unit

FIGS. 5A through 5C are drawings illustrating an example of a structure of the attachment unit 40 which is attached to the subject 500. FIG. 5A is a plan view. FIG. 5B is a bottom view. FIG. 5C is a cross-sectional view along an A-A line in FIG. 5A. FIG. 6 is a cross-sectional view illustrating an example of a state in which the attachment unit 40 is attached to the subject 500. It should be noted that, in figures other than the cross-sectional view, illustration of an electrically-conductive material 390 is omitted (it will be the same in the following figures).

Referring to FIGS. 5A-5C and FIG. 6, in the attachment unit 40, a part of the electrode 310 included in the nerve stimulation apparatus 30 is arranged. In examples of FIGS. 5A-5C, seven stimulation negative electrodes 311 (311A-311G) and the stimulation positive electrode 312 are arranged. The number of the stimulation negative electrodes 311 is not limited to seven. The necessary number of the stimulation negative electrodes 311 may be arranged accordingly.

The attachment unit 40 includes a band 41, a movable unit 42 disposed on the front surface of the band 41, and a three-dimensional structure 43 disposed on the movable unit 42. It should be noted that the front surface is in touch with the living body (arm of the subject, etc.)

The band 41 is a member for attaching and fixing the stimulation negative electrodes 311 and the stimulation positive electrode 312 to an arm of the subject 500, etc., and has flexibility. In order to change the position of the stimulation negative electrodes 311 according to the position of the nerve, the movable unit 42 has a structure in which the stimulation negative electrodes 311 arranged on the three-dimensional structure 43 are capable of sliding in a longitudinal direction on the band 41 together with the three-dimensional structure 43. In other words, the movable unit 42 causes the stimulation negative electrodes 311 to slide on the band 41, and causes the positional relationship between the stimulation negative electrodes 311 and the stimulation positive electrode 312 to be changeable. It should be noted that the movable unit 42 may be included if necessary.

The three-dimensional structure 43 is a member, disposed under the bottom of the stimulation negative electrodes 311, which is convex on the side of the skin of the subject 500. The three-dimensional structure 43 has a function for causing the stimulation negative electrodes 311 to get closer to the nerve by pressing the stimulation negative electrodes 311 against the skin when the attachment unit 40 is attached to an arm, etc., of the subject 500.

An input negative electrode 44 is projecting on the back surface of the band 41. The selection circuit 330 may be mounted on the front surface of the band 41. An input of the selection circuit 330 is connected to the input negative electrode 44, and an output of the selection circuit 330 is connected to each of the stimulation negative electrodes 311 (311A to 311G). The selection circuit 330 may include, for example, a relay or a semiconductor switch.

The input negative electrode 44 is a knob for connecting to an external cable when the current supply unit 320 supplies a stimulation current and when the PC 350 transmits to the selection circuit 330 an instruction for which stimulation negative electrode 311 should be selected. In other words, the input negative electrode 44 is connected to the stimulation negative electrode 311 which is selected by the selection circuit 330 based on the instruction from the PC 350. Further, the input negative electrode 44 is a part of a channel in which a stimulation current from the current supply unit 320 flows.

The stimulation positive electrode 312 is disposed on the front surface of the band 41. An input positive electrode 45 is projecting on the back surface of the band 41. The input positive electrode 45 is a knob for connecting to a cable when a stimulation current is supplied from the current supply unit 320, and is electrically connected to the stimulation positive electrode 312. It is preferable that a distance between the stimulation positive electrode 312 and the stimulation negative electrode 311, of the stimulation negative electrodes 311 (311A to 311G), that is closest to the stimulation positive electrode 312 is equal to or more than 2 cm.

It should be noted that it is preferable to have the electrically-conductive material 390 at parts of the stimulation negative electrodes 311 and the stimulation positive electrode 312 which parts are in touch with an arm, etc., of the subject 500. With the above arrangement, it is possible to lower contact resistances between the stimulation negative electrodes 311 and the surface of a living body (surface of an arm, etc., of the subject 500), and between the stimulation positive electrode 312 and the surface of a living body, and thus, it is easier to inject a stimulation current into the nerves. As the electrically-conductive material 390, for example, an electrically-conductive gel, a silver chloride, etc., may be used.

Band fixing tapes 46 and 47 are disposed on the front surface and the back surface of the band 41, respectively. The band fixing tapes 46 and 47 are used for joining both ends of the band 41 when the band 41 is wound around an arm, etc., of the subject 500.

It should be noted that the three-dimensional structure 43 may have a cross-sectional shape of a convex portion of a semicircular column (so-called "kamaboko" shape) as illustrated in FIG. 7A, may have a convex portion of a frustum of a cone as illustrated in FIG. 7B, or may have a convex portion of other shapes. The point is, whatever the structure of the three-dimensional structure 43 may be, the structure can be anything as long as the structure has a function for causing the stimulation negative electrodes 311 to be pressed against the skin and causing the stimulation negative electrodes 311 to get closer to the nerve.

Further, as illustrated in FIG. 8, planar shapes of the stimulation negative electrodes 311 (311A to 311G) may be, for example, circles. In this case, it is preferable that the center-to-center distance S of adjacent stimulation negative electrodes 311 be less than 3 mm. If the center-to-center distance S of adjacent stimulation negative electrodes 311 is equal to or greater than 3 mm, then the nerve selectivity may be degraded.

Further, it is preferable that an area of each of the stimulation negative electrodes 311 (311A to 311G) be equal to or greater than 12 mm$^2$. In the case where the planar shape of each stimulation negative electrode 311 is a circle, it is preferable that the diameter φ of each stimulation negative electrode 311 be equal to or greater than 4 mm. The above arrangement is preferable because, in the case where the area of each of the stimulation negative electrodes 311 (311A to 311G) is less than 12 mm$^2$ (the diameter φ of each stimulation negative electrode 311 is less than 4 mm in the case where the planar shape of each stimulation negative electrode 311 is a circle), the pain becomes severe and it becomes difficult to perform measurement of the spinal cord evoked magnetic field.

It should be noted that the planar shape of each of the stimulation negative electrodes 311 (311A to 311G) may be other than the circle. The planar shape of each of the stimulation negative electrodes 311 (311A to 311G) may be, for example, an oblong or a polygon (a hexagon, etc.) Further, arrangement of the stimulation negative electrodes 311 (311A to 311B) is not limited to an example of FIG. 8, and may be determined appropriately.

FIG. 9 is a cross-sectional view illustrating an example of a specific structure of the movable unit 42. The movable unit 42 illustrated in FIG. 9 includes a foundation 421, a belt 422 and a gear 423. The foundation 421 is a plate-shaped member for fixing the band 41 to the movable unit 42. The belt 422 is a flexible film-shaped member, to the upper surface of which the stimulation negative electrodes 311 are fixed, which slides according to the rotation of the gear 423.

For example, a small motor for rotating the gear 423 may be included, a driving signal may be supplied from the current supply unit 320 to the motor for rotating the gear 423, and the belt 422 of the movable unit 42 may be caused to slide. With the above arrangement, it is possible for the stimulation negative electrodes 311 on the belt 422 to be caused to slide in a longitudinal direction of the band 41.

By including the movable unit 42, it is possible to change arbitrarily the positional relationship between the stimulation negative electrodes 311 and the stimulation positive electrode 312 according to the thickness of an arm, etc., of the subject 500. As a result, it is possible to improve the nerve selection accuracy and to stimulate the nerve accurately.

Measurement Example

Seven stimulation negative electrodes 311 (311A to 311G) were arranged as illustrated in FIG. 8. Further, the diameter φ of each of the stimulation negative electrodes 311 was equal to or greater than 4 mm. Myoelectric signals with the stimulation negative electrode 311 were obtained, with which electrode a signal appears at about 10 ms indicated the maximum value (hereinafter, referred to as the maximum myoelectric signal) in the case where the center-to-center distance S of adjacent stimulation negative electrodes 311 was equal to or greater than 3 mm, and in the case where the center-to-center distance S of adjacent stimulation negative electrodes 311 was less than 3 mm, respectively. Regarding the stimulation current, the current value was 7 mA and the frequency was 5 Hz.

Further, the attachment unit 40 was attached and detached every time the measurement was performed. Data was obtained 100 times for every measurement. According to the average of 100 data sets, in the case where the diameter φ of each of the stimulation negative electrodes 311 was equal to or greater than 4 mm and the center-to-center distance S of adjacent stimulation negative electrodes 311 was equal to or greater than 3 mm, the maximum myoelectric signal appearing at about 10 ms was about 0.25 mV as illustrated in FIG. 10A.

On the other hand, in the case where the diameter φ of each of the stimulation negative electrodes 311 was equal to or greater than 4 mm and the center-to-center distance S of adjacent stimulation negative electrodes 311 was less than 3 mm, the maximum myoelectric signal appearing at about 10 ms was about 1.0 mV as illustrated in FIG. 10B.

In other words, when the maximum myoelectric signal (at about 10 ms) in the case where the center-to-center distance S of adjacent stimulation negative electrodes 311 was equal to or greater than 3 mm is compared with the maximum myoelectric signal (at about 10 ms) in the case where the center-to-center distance S of adjacent stimulation negative electrodes 311 was less than 3 mm, an about four times greater myoelectric signal was obtained in the case of less than 3 mm than the case of equal to or greater than 3 mm.

It should be noted that when the electromyogram of FIG. 10B was obtained, seven stimulation negative electrodes 311 (311A to 311G) were arranged as illustrated in FIG. 8, the diameter φ of each of the stimulation negative electrodes 311 (311A to 311G) was 4 mm, and the center-to-center distance S of the adjacent stimulation negative electrodes 311 was 2 mm.

It should be noted that in the arrangement of FIG. 8, the myoelectric signal measurement was also tried in the case where the diameter φ of each of the stimulation negative electrodes 311 was less than 4 mm. However, in the case where the diameter φ of each of the stimulation negative electrodes 311 was less than 4 mm, the pain to the subject 500 was too strong. Therefore no nerve stimulation was applied and no measurement was made.

FIG. 11 is a drawing illustrating an example of a relationship between myoelectric measurement and the stimulation negative electrodes when electrical stimulation was applied to an arm of the subject 500. According to the measurement result described above, it can be said that the diameter φ of the stimulation negative electrode 311 determines the degree of pain. Further, it can be said that the center-to-center distance S of the adjacent stimulation negative electrodes 311 determines whether the nerve selectivity is good or bad.

Further, as illustrated in the upper left side of FIG. 11, in the case where the diameter φ of the stimulation negative electrode 311 was equal to or greater than 4 mm and the center-to-center distance S of the adjacent stimulation negative electrodes 311 was less than 3 mm, there was no pain and the nerve selectivity was good (in other words, the spatial resolution of the stimulation negative electrode 311 was appropriate). As a result, a good myoelectric waveform as illustrated in FIG. 10B was obtained.

Further, as illustrated in the upper right side of FIG. 11, in the case where the diameter φ of the stimulation negative electrode 311 was equal to or greater than 4 mm and the center-to-center distance S of the adjacent stimulation negative electrodes 311 was equal to or greater than 3 mm, the nerve selectivity was bad. As a result, the myoelectric signal was weaker than the case where the center-to-center distance S of the adjacent stimulation negative electrodes 311 was less than 3 mm, and the myoelectric waveform as illustrated in FIG. 10A was obtained.

Further, as illustrated in the lower left side and the lower right side of FIG. 11, in the case where the diameter φ of each of the stimulation negative electrodes 311 was less than 4 mm, the pain to the subject 500 was too severe to apply the nerve stimulation regardless the size of the center-to-center distance S of the adjacent stimulation negative electrodes 311, and no measurement was made.

As described above, a nerve stimulation apparatus 30 according to an embodiment includes separately the stimulation unit (the stimulation negative electrodes and the stimulation positive electrode) and the detection unit, and uses an electromyograph in the detection unit. Further, a current is supplied to multiple electrodes arranged on the skin, and electrical stimulation is applied to the nerve of a living body. Further, measurement results of muscle activities are received from the electromyograph which measures activities of muscles governed by the stimulated nerve, and it is determined with which electrodes activities of muscles are sufficiently strong. As a result, it is possible to improve the nerve selection accuracy and to stimulate the target nerve accurately. In other words, it is possible to provide a nerve stimulation apparatus in which the accuracy of selecting the nerve stimulation electrode is improved.

Further, by including separately the stimulation unit and the detection unit, it is possible to detect a current flowing in the low resistance nerve with high purity. Further, by using the electromyograph which is capable of detecting with high sensitivity muscle activities according to a current flowing in the nerve, it is possible to make sure that the nerve is accurately stimulated. In other words, in order to accurately stimulate the nerve, it is possible to accurately detect the nerve. Further, the pain to the subject is not too strong, and thus, it is possible to realize a measurement environment which is not uncomfortable.

The preferred embodiments have been described. However, the embodiments are not limited to as described above, and various modifications and replacements may be applied to the above embodiments without departing from the scope of claims.

For example, in an embodiment described above, an example of a spinal cord evoked magnetic field measurement system for detecting a current flowing in the spinal cord as a magnetic field (spinal cord meter) is illustrated, in which system a nerve stimulation apparatus according to an embodiment and a magnetism measurement apparatus are included. Embodiments are not limited to the above. For example, it is possible to realize a biomagnetic field measurement system such as a mannetoen-cephalography, MEG including a nerve stimulation apparatus according to an embodiment and a magnetism measurement apparatus.

Further, in an embodiment described above, in the magnetism measurement apparatus, an example is illustrated in which a SQUID sensor is used for forming a sensor array, which is not limited to using a SQUID sensor. In the magnetism measuring apparatus, as a sensor for forming a sensor array, for example, an atomic magnetometer (AMM element), a magnetoresistive element (MR element), a magnetic impedance element (MI sensor), etc., may be used.

Further, a nerve stimulation apparatus according to an embodiment is not limited to be applied to a spinal cord evoked magnetic field measurement system, but may be applied to typical nerve function tests such as somatosensory evoked potential (SEP) tests and motor nerve conduction velocity (MCV) tests.

The present application is based on and claims the benefit of priority of Japanese Priority Application No. 2015-232936 filed on Nov. 30, 2015, the entire contents of which are hereby incorporated by reference.

DESCRIPTION OF THE REFERENCE NUMERALS

1 Spinal cord evoked magnetic field measurement system
10 Magnetism measurement apparatus
11 SQUID sensor array
12 Signal processing unit
20 Cryogenic container
30 Nerve stimulation apparatus
40 Attachment unit
41 Band
42 Movable unit
43 Three-dimensional structure
44 Input negative electrode
45 Input positive electrode
46, 47 Band fixing tape
61, 62 Signal line
100 Magnetism shielded room
110 Door
150 Table
201 Protrusion unit
310 Electrode
311, 311A to 311G Stimulation negative electrode
312 Stimulation positive electrode
313 Detection negative electrode
314 Detection positive electrode
320 Current supply unit
330 Selection circuit
340 Electromyograph
350 PC
390 Electrically-conductive material
421 Foundation
422 Belt
423 Gear
500 Subject
1001, 1002 Hole

The invention claimed is:

1. A nerve stimulation apparatus for detecting nerve activities from a body surface and applying stimulation, the nerve stimulation apparatus comprising:
a stimulation apparatus, including a plurality of electrodes, a three-dimensional structure that has a convex portion on at least one side, and a current supply unit for supplying a current to the electrodes, which are configured to provide the current percutaneously to a living body to stimulate a target nerve;
a measurement apparatus configured to measure activities of muscles governed by the target nerve stimulated by the stimulation apparatus, or the nerve activities of the target nerve itself; and
an information processing apparatus configured to determine, based on a measurement result of the nerve activities obtained from the measurement apparatus, which electrode is capable of providing the target nerve activities equal to or greater than a desired value, wherein the electrodes include a plurality of stimulation negative electrodes, a center-to-center distance of adjacent ones of the stimulation negative electrodes is less than 3 mm, an area of each of the stimulation negative electrodes is equal to or greater than 12 mm$^2$, and the stimulation negative electrodes are arranged on the convex portion of the three-dimensional structure.

2. The nerve stimulation apparatus according to claim 1, wherein the stimulation apparatus includes a selection circuit, and the current supply unit supplies the current to the electrode selected by the selection circuit.

3. The nerve stimulation apparatus according to claim 1, wherein the three-dimensional structure has a semicircular column shape.

4. The nerve stimulation apparatus according to claim 1, wherein the three-dimensional structure has a shape of a frustum of a cone.

5. The nerve stimulation apparatus according to claim 1, further comprising:

a band configured to attach and fix the electrodes to the living body and include a movable unit disposed on a surface of a side of the band which side is in contact with the living body, wherein the stimulation negative electrodes are arranged on the movable unit.

6. The nerve stimulation apparatus according to claim 5, wherein the electrodes include a stimulation positive electrode, and the movable unit causes the stimulation negative electrodes to slide on the band and causes a positional relationship between the stimulation negative electrodes and the stimulation positive electrode to be changed.

7. A biomagnetic field measurement system comprising:
a nerve stimulation apparatus according to claim 1; and
a magnetism measurement apparatus configured to measure magnetic fields evoked in the living body by electrical stimulation of the nerve stimulation apparatus.

8. A nerve stimulation apparatus for detecting nerve activities from a body surface and applying stimulation, the nerve stimulation apparatus comprising:

a stimulation apparatus, including a plurality of electrodes and a current supply unit for supplying a current to the electrodes, which are configured to provide the current percutaneously to a living body to stimulate a target nerve;

a measurement apparatus configured to measure activities of muscles governed by the target nerve stimulated by the stimulation apparatus, or the nerve activities of the target nerve itself; and an information processing apparatus configured to determine, based on a measurement result of the nerve activities obtained from the measurement apparatus, which electrode is capable of providing the target nerve activities equal to or greater than a desired value, wherein the electrodes include a plurality of stimulation negative electrodes and a stimulation positive electrode, the apparatus further includes a band configured to attach and fix the electrodes to the living body and include a movable unit disposed on a surface of a side of the band which side is in contact with the living body, wherein the stimulation negative electrodes are arranged on the movable unit, and the movable unit causes the stimulation negative electrodes to slide on the band and causes a positional relationship between the stimulation negative electrodes and the stimulation positive electrode to be changed.

* * * * *